United States Patent
Takeuchi (10) Patent No.: US 6,999,170 B2
(45) Date of Patent: Feb. 14, 2006

(54) OPTICAL ANALYSIS APPARATUS AND PARTICLE COUNTING METHOD

(75) Inventor: Kazuhiro Takeuchi, Touyo (JP)

(73) Assignee: Matsushita Electric Industrial Co., Ltd., (JP)

( * ) Notice: Subject to any disclaimer, the term of this patent is extended or adjusted under 35 U.S.C. 154(b) by 0 days.

(21) Appl. No.: 10/973,399

(22) Filed: Oct. 27, 2004

(65) Prior Publication Data
US 2005/0094140 A1    May 5, 2005

(30) Foreign Application Priority Data
Oct. 30, 2003 (JP) ............... 2003-369741
Sep. 24, 2004 (JP) ............... 2004-276266

(51) Int. Cl.
*G01N 15/02* (2006.01)
(52) U.S. Cl. ............ 356/335; 356/336; 356/337; 356/338; 356/341
(58) Field of Classification Search ........ 356/335–343, 356/72–73; 250/574–575
See application file for complete search history.

(56) References Cited

U.S. PATENT DOCUMENTS

| | | | | |
|---|---|---|---|---|
| 4,071,298 A | * | 1/1978 | Falconer | 356/73 |
| 5,037,202 A | * | 8/1991 | Batchelder et al. | 356/336 |
| 5,534,999 A | * | 7/1996 | Koshizuka et al. | 356/338 |
| 5,561,515 A | * | 10/1996 | Hairston et al. | 356/28 |
| 6,411,377 B1 | * | 6/2002 | Noguchi et al. | 356/237.4 |

FOREIGN PATENT DOCUMENTS

| | | |
|---|---|---|
| JP | 10-504397 | 4/1998 |
| WO | WO 96/09548 | 3/1996 |

* cited by examiner

*Primary Examiner*—Gregory J. Toatley, Jr.
*Assistant Examiner*—Sang H. Nguyen
(74) *Attorney, Agent, or Firm*—Steptoe & Johnson LLP (57) ABSTRACT

Differential signals and sum signals are extracted from a detection signal of passing light detected when a light beam emitted to an analysis optical disc passes through a particle on the disc. Presence of the particle is decided based on the differential signals, effectiveness of counting particles is decided based on the sum signals, and the decision results are stored. The stored decision results are scanned by using a scanning window corresponding to a minimum size of measured objects, particles having the minimum size are detected, and the number of detected particles is stored. Subsequently, the stored decision results are scanned using a scanning window corresponding to a size larger by one scan than the maximum size of the measured objects, particles having a size larger by one scan than the maximum size are detected, and the number of detected particles is stored. Finally, the number of detected particles within a certain size range is determined based on a difference between the stored numbers of detected particles.

4 Claims, 8 Drawing Sheets

OPTICAL ANALYSIS APPARATUS AND PARTICLE COUNTING METHOD

FIELD OF THE INVENTION

The present invention relates to an optical analysis apparatus for optically analyzing particles disposed in a specific area of an analysis optical disc, and a method of counting the particles.

BACKGROUND OF THE INVENTION

For example, as a known optical analysis apparatus, National Publication of International Patent Application No. 10-504397 discloses a sample analysis apparatus for optically measuring (inspecting) a sample disposed in a specific area of an analysis optical disc.

The sample analysis apparatus has an analysis optical disc which is a circular disc where particles (e.g., antibodies, blood plasma, and blood cells) are combined as a sample of a measured object. The disc comprises lower and upper layers, which are made of transparent plastic materials, and a metal foil layer having a light-reflecting surface between the layers. The sample analysis apparatus moves, relative to the circular disc, an inspection optical block disposed above the circular disc and an extraction optical block disposed below the circular disc, and measures the particles disposed in a specific area of the circular disc.

The inspection optical block is constituted of a laser diode, a lens for focusing a light beam, which has been emitted from the laser diode, on a surface of the circular disc, a polarizing prism for polarizing by 90 degrees a light beam having been reflected from the light-reflecting surface, and a detector for detecting reflected light which has been inputted via the polarizing prism.

The extraction optical block is constituted of a detector for extracting light (passing light) when a light beam having been emitted from the laser diode of the inspection optical block passes through the circular disc.

The emitted light beam is affected by the particles and passing light inputted to the detector of the extraction optical block is reduced in effect. Thus, the particles of the circular disc are detected by collecting and analyzing passing light inputted to the detector of the extraction optical block. Further, two-dimensional memory is provided for the radius direction and track direction of the circular disc, and a position where the particle is detected is marked and stored for each scan.

In the known optical analysis apparatus, by using the two-dimensional memory after measurements, particles serving as measured objects within a certain size range are selected from particles of various sizes in the specific area of the analysis optical disc and the number of detected particles is determined.

The following will describe an example where the number of particles ranging in size from three to six tracks is determined on the circular disc where particles ranging in size from three to seven tracks are disposed.

First, the two-dimensional memory is scanned by using a 3×A scanning window which corresponds to a particle of the minimum size, and particles having a size of three tracks are detected from the two-dimensional memory. Subsequently, the two-dimensional memory is scanned by using a 7×A scanning window which corresponds to a size which is one track larger than the maximum size of particles to be detected, and particles having a size of seven tracks are detected from the two-dimensional memory. "A" in the scanning window represents a size corresponding to a displacement of a detection position in the track direction. The displacement is caused by uneven rotation of the circular disc and uneven detection of signals.

However, particles ranging in size from three to six tracks cannot be correctly counted simply based on a difference between the number of detected particles having a size of three tracks and the number of detected particles having a size of seven tracks. This is because the number of detected particles having a size of three tracks includes the number of detected particles having a size of six tracks, which is a multiple of three tracks. Hence, it is necessary to scan the two-dimensional memory by using a 6×A scanning window corresponding to particles having a size of six tracks, which is a multiple of three tracks, and detect particles having a size of six tracks from the two-dimensional memory. By determining a difference between the number of detected particles having a size of seven tracks and the number of detected particles having a size of six tracks based on the number of detected particles having a size of three tracks, the true number of detected particles ranging in size from three to six tracks is determined.

In this way, when particles serving as measured objects within a certain size range are selected and the number of detected particles is determined, it is necessary to scan the same tracks having the particles again and again while frequently changing the size of the scanning window for selecting the particles, so that much time is spent in the detection and counting of particles and the particles cannot be counted correctly.

DISCLOSURE OF THE INVENTION

It is an object of the present invention to provide a precise and fast optical analysis apparatus and a particle counting method by performing only the minimum number of scans on a track having a particle serving as a measured object, without frequently changing the size of a scanning window for selecting particles.

In order to attain this object, according to the present invention, when a light beam, which is emitted to an analysis optical disc and is scanned thereon, passes through particles on the disc, passing light is received and detected by a photodetector. Differential signals and sum signals are extracted from a detection signal of the received passing light. The presence of a particle is decided based the differential signal and the decision result is stored in differential signal memory. The effectiveness of counting a particle is decided based on the sum signal and the decision result is stored in sum signal memory. The differential signal memory and the sum signal memory are scanned by using a scanning window corresponding to the minimum size of a measured object, particles having the minimum size are detected, and the number of detected particles is stored. Subsequently, scanning is performed by using a scanning window corresponding to a size which is larger by one scan than the maximum size of the measured object, particles larger than the maximum size by one scan are detected, and the number of detected particles is stored. Finally, the number of detected particles within a certain size range is determined based on a difference between the stored numbers of detected particles.

DESCRIPTION OF THE EMBODIMENT

The following will describe an embodiment of the present invention in accordance with the accompanying drawings.

Figure 1:
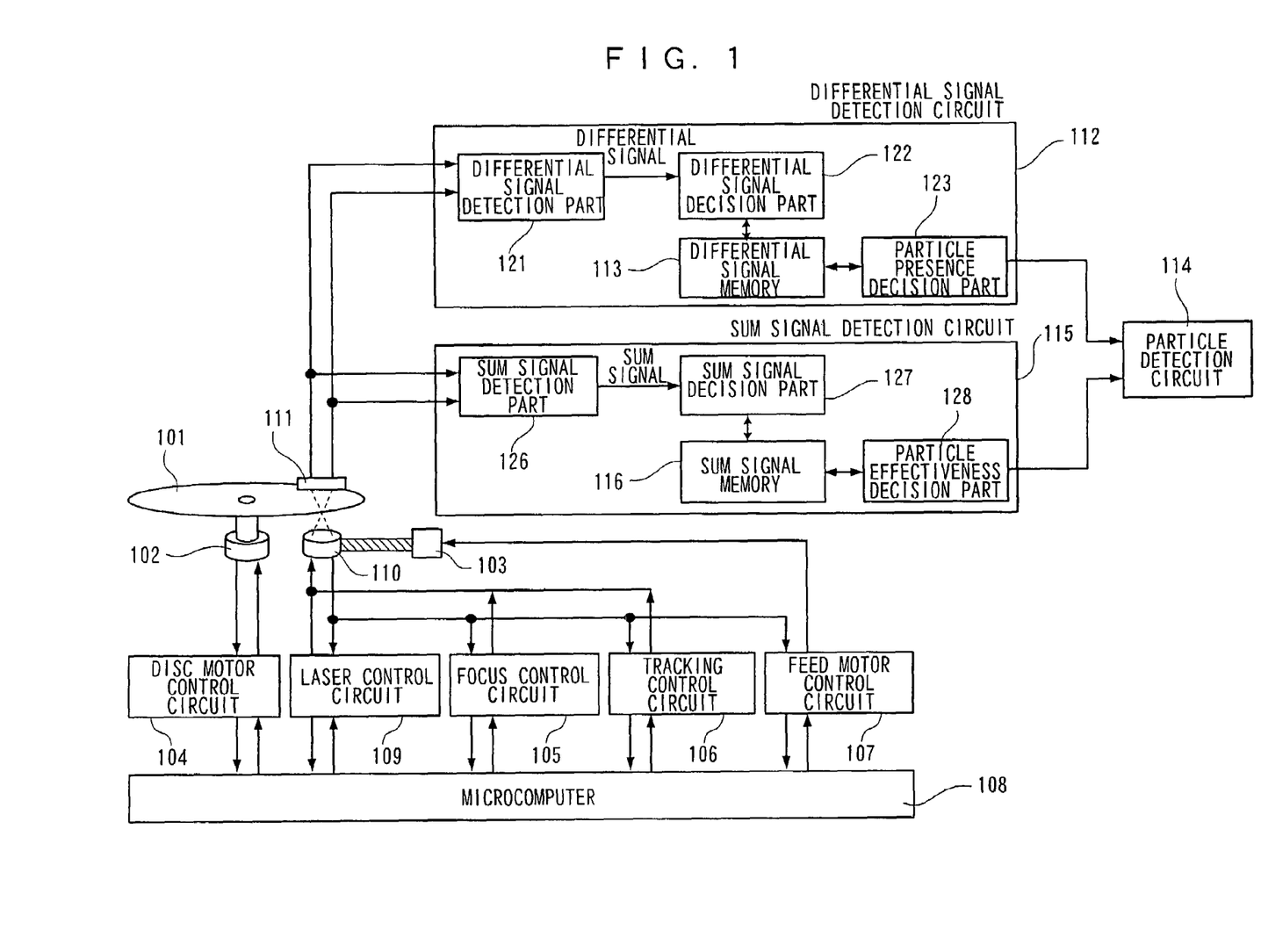
FIG. 1 is a structural diagram showing an optical analysis apparatus according to an embodiment of the present invention.

FIG. 1 is a structural diagram showing an optical analysis apparatus according to the embodiment of the present invention.

In FIG. 1, reference numeral 101 denotes an analysis optical disc on which particles serving as measured objects are disposed. The analysis optical disc is an optical disc which has a spiral track like an optical disc such as a CD-R. The analysis optical disc 101 is attached to a disc motor 102. The disc motor 102 is driven in response to a control signal from a disc motor control circuit 104 for controlling the number of revolutions, so that the analysis optical disc 101 is rotated.

The disc motor 102 and the disc motor control circuit 104 constitute a disc rotating device for rotating the analysis optical disc 101.

Further, a pickup device 110 is provided at a predetermined position of the analysis optical disc 101. The pickup device 110 has a laser light source which emits a light beam through an object lens as a light-emitting device and a reflected light detector which detects light reflected from a disc surface. Signals detected by the reflected light detector of the pickup device 110 are inputted to a focus control circuit 105, a tracking control circuit 106, a feed motor control circuit 107, and a laser control circuit 109.

The laser control circuit 109 keeps a stable radiation power of a light beam from the laser light source of the pickup device 110.

The focus control circuit 105 moves the object lens of the pickup device 110 in the direction of the optical axis to control a focused state.

The tracking control circuit 106 horizontally moves the object lens of the pickup device 110 to control a tracking state.

The feed motor control circuit 107 horizontally moves the pickup device 110 by means of a feed motor 103.

The disc motor control circuit 104, the focus control circuit 105, the tracking control circuit 106, the feed motor control circuit 107, and the laser control circuit 109 are subjected to centralized control by a microcomputer 108. For example, a servo control signal is outputted and scan control is performed to move the laser light source.

A scanner is formed in which the pickup device 110 is driven by the feed motor 103 and the feed motor control circuit 107 and a light beam is scanned along a track of the analysis optical disc 101.

As a light detector, a bi-cell photo detector 111 is provided which is disposed on the opposite side of the analysis optical disc 101 from the pickup device 110, is horizontally moved with the pickup device 110, and receives passing light of a light beam which is emitted from the laser light source of the pickup device 110 to the analysis optical disc 101. Since the photodetector 111 is divided into two, two light-receiving parts are formed which have a boundary substantially orthogonal to a direction of scanning a light beam. The photodetector 111 is not always divided into two. The photodetector 111 may be further divided substantially orthogonally and a light beam may be received by at least two light-receiving parts.

Detection signals of passing light having been received by the bi-cell photodetector 111 is inputted to a differential signal detection circuit 112 and a sum signal detection circuit 115.

When a light beam is traced along the track of the analysis optical disc 101, the differential signal detection circuit 112 detects a particle serving as a measured object, by means of the detection signal of passing light detected during the passage of the particle. The detection signal is obtained from the bi-cell photodetector 111. The differential signal detection circuit 112 is constituted of a differential signal detection part 121, a differential signal decision part 122, differential signal memory 113, and a particle presence decision part 123.

Figure 2A:
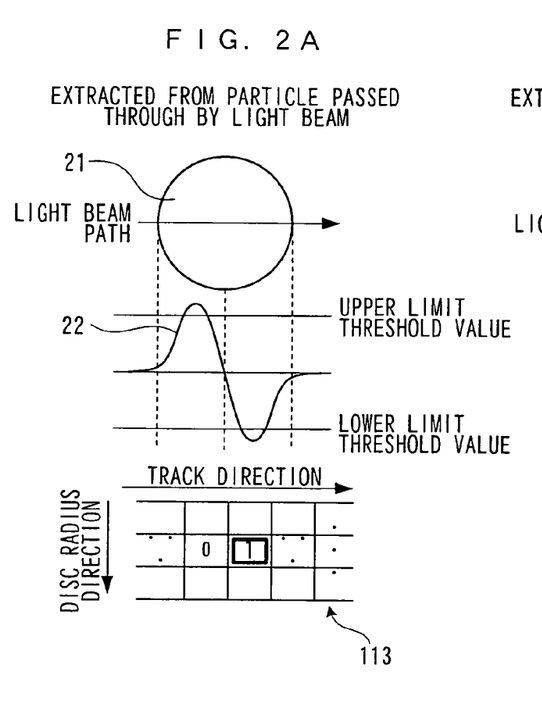
FIGS. 2A to 2D each shows an example of particle detection in the optical analysis apparatus.
Figure 2B:
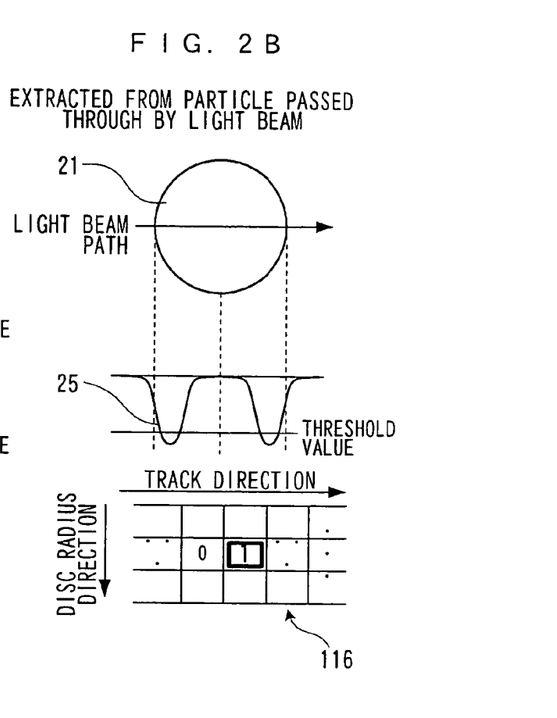
Figure 2C:
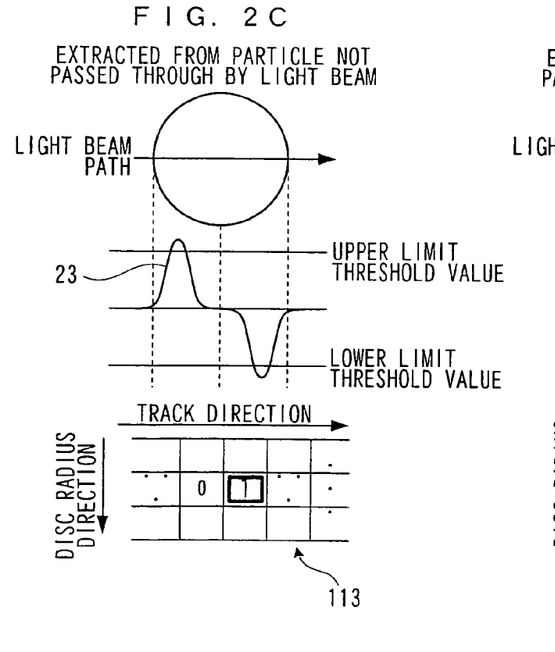

The differential signal detection part 121 extracts a differential signal obtained by differentiating the detection signal of passing light from the bi-cell photodetector 111 and outputs the differential signal to the differential signal decision part 122. FIG. 2A shows an example of a differential signal 22 extracted from a particle passing through a light beam. FIG. 2C shows an example of a differential signal 23 extracted from a particle not passing through a light beam.

When a light beam is traced (scanned) along the track of the analysis optical disc 110, the differential signal decision part 122 decides the presence of a particle based on the amplitudes of the differential signals 22 and 23 extracted by the differential signal detection part 121. A specific upper/lower limit threshold value (first threshold value) is used as a criterion for deciding the presence of a particle. The decision result is stored in the differential signal memory 113. That is, as shown in FIGS. 2(a) and 2(c), when it is decided that a particle 21 is scanned on the analysis optical disc 101, a mark "1" indicating the presence of the particle is stored in the differential signal memory 113. When it is decided that the particle is not present, a presence result storing operation is performed to store in the differential signal memory 113 a mark "0" indicating the absence of the particle. The differential signal memory 113 is constituted of a two-dimensional memory array. The column direction represents the track direction of the analysis optical disc 101 and the row direction represents the radius direction of the analysis optical disc 101.

The particle presence decision part 123 scans the differential signal memory 113, in which data on the presence of a particle is stored by the differential signal decision part 122, by using a first scanning window of M×N corresponding to a particle serving as a measured object within a certain size range. The particle presence decision part 123 extracts an array of mark "1" indicating the presence of the particle, decides whether a particle serving as a measured object within a certain size range is present or not, and outputs the decision to a particle detection circuit 114. M in the first scanning window is set according to the size of a measured particle in the radius direction of the disc. N in the first scanning window represents a size corresponding to a displacement of a detection position in the track direction. The displacement is caused by uneven rotation of the analysis optical disc 101 and uneven detection of signals. A value larger than the displacement range of the detection position is set for N. Hence, even when the detection position is displaced on each track, data can be handled so as to be detected from the same particle.

The sum signal detection circuit 115 decides the effectiveness of a particle by using a detection signal of passing light from the bi-cell photodetector 111. As shown in FIG. 1, the sum signal detection circuit 115 is constituted of a sum signal detection part 126, a sum signal decision part 127, sum signal memory 116, and a particle effectiveness decision part 128.

Figure 2D:
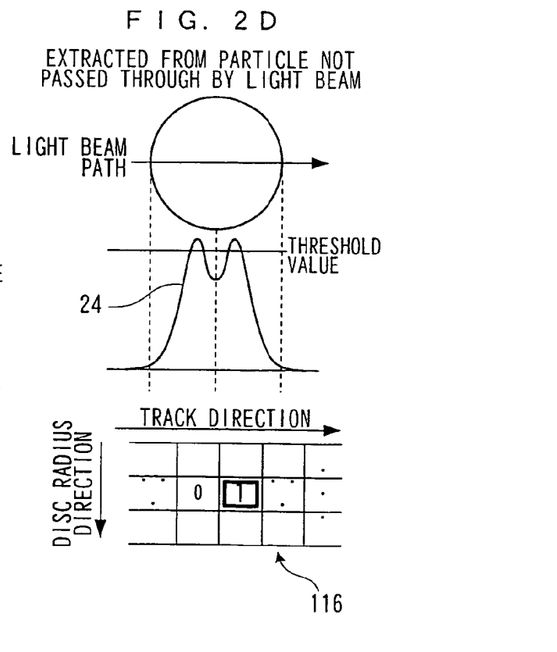
Figure 3:
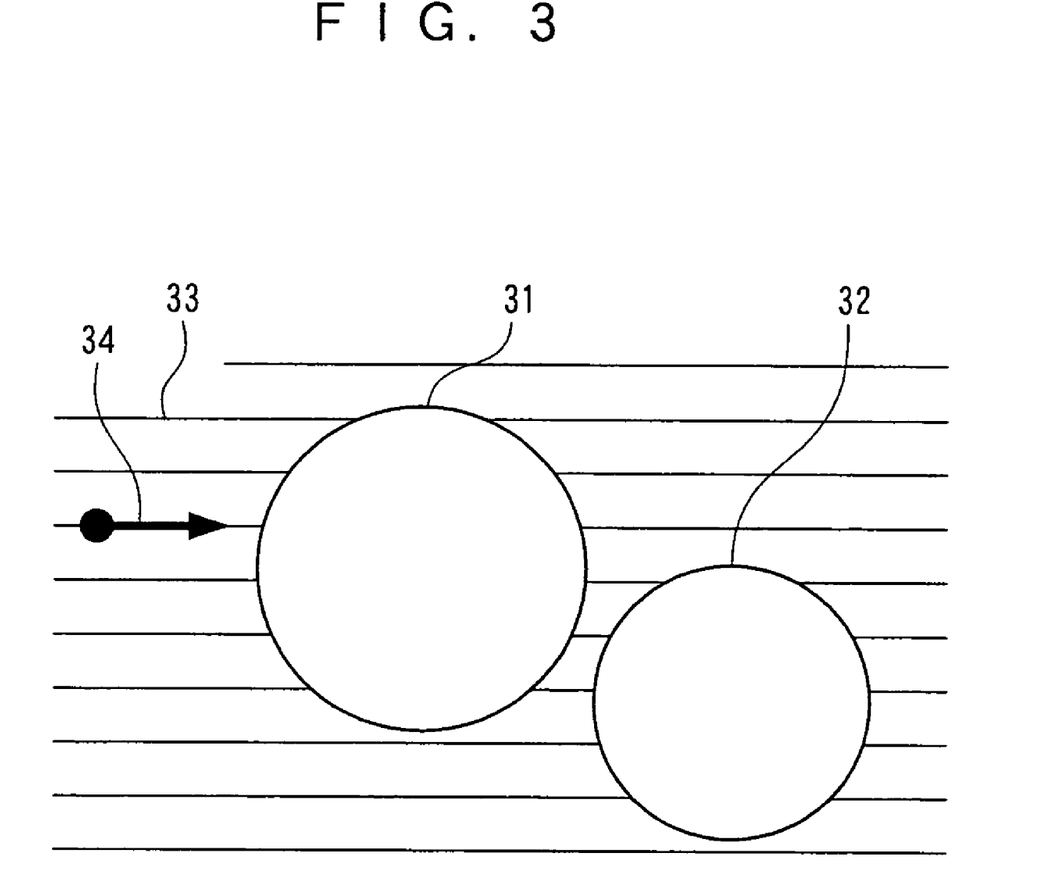
FIG. 3 is a diagram showing an example of a particle size measured in the optical analysis apparatus.

When a light beam passes through a particle, the sum signal detection part 126 extracts a sum signal, which is obtained by summing detection signals of passing light from the bi-cell photodetector 111, and outputs the sum signal to the sum signal decision part 127. FIG. 2B shows an example of a sum signal 25 extracted from a particle passing through a light beam. FIG. 2D shows an example of a sum signal 24 extracted from a particle not passing through a light beam.

When a light beam is traced along the track of the analysis optical disc 101, the sum signal decision part 127 decides whether the analysis optical disc 101 has a countable particle or not, that is, the effectiveness of a particle based on the amplitudes of the sum signals 25 and 24 extracted by the sum signal detection part 126. A specific threshold value (second threshold value) is used as a criterion for deciding the effectiveness of counting a particle. Then, the sum signal decision part 127 stores the result in the sum signal memory 116. That is, as shown in FIGS. 2(b) and 2(d), a result on effectiveness is stored as below: when the signal level of the sum signals 25 and 24 is higher than or equal to a threshold value, it is decided that a traced track has the countable and effective particle 21 for each scan on the analysis optical disc 101, and the mark "1" indicating the presence of the countable particle is stored in the sum signal memory 116. When the signal level of the sum signals 25 and 24 is lower than the threshold value, it is decided that the traced track has no countable and effective particle, and the mark "0" indicating the absence of a countable particle is stored in the sum signal memory 116. The sum signal memory 116 is constituted of a two-dimensional memory array. The column direction represents the track direction of the analysis optical disc 101 and the row direction represents the radius direction of the analysis optical disc 101.

By using a second scanning window of m×n for deciding the effectiveness of a particle, the particle effectiveness decision part 128 extracts a change from the mark "0" indicating the absence of a countable particle to the mark "1" indicating the presence of a countable particle. The change is extracted from the sum signal memory 116 in which data on the effectiveness of a particle is stored by the sum signal decision part 127. Then, the particle effectiveness decision part 128 decides the effectiveness of counting a particle and outputs the result to the particle detection circuit 114 (the detail will be described later). A value is set for "m" in the scanning window to capture a change from the mark "0" to the mark "1" in the radius direction of the disc. "n" in the scanning window represents a size corresponding to a displacement of a detection position in the track direction. The displacement is caused by uneven rotation of the circular disc 101 and uneven detection of signals. The value n is equal to N in the scanning window of M×N used in the particle presence decision part 123.

By using the presence/absence decision result obtained from the differential signal detection circuit 112 and the effectiveness decision result obtained from the sum signal detection circuit 115, the particle detection circuit 114 counts a particle serving as a measured object when it is decided that the particle is present and effective.

The following will specifically discuss a method of deciding the presence/absence of a particle in the particle presence decision part 123 of the differential signal detection circuit 112, a method of deciding the effectiveness of a particle in the particle effectiveness decision part 128 of the sum signal detection circuit 115, and the operations of the particle detection circuit 114.

Figure 4:
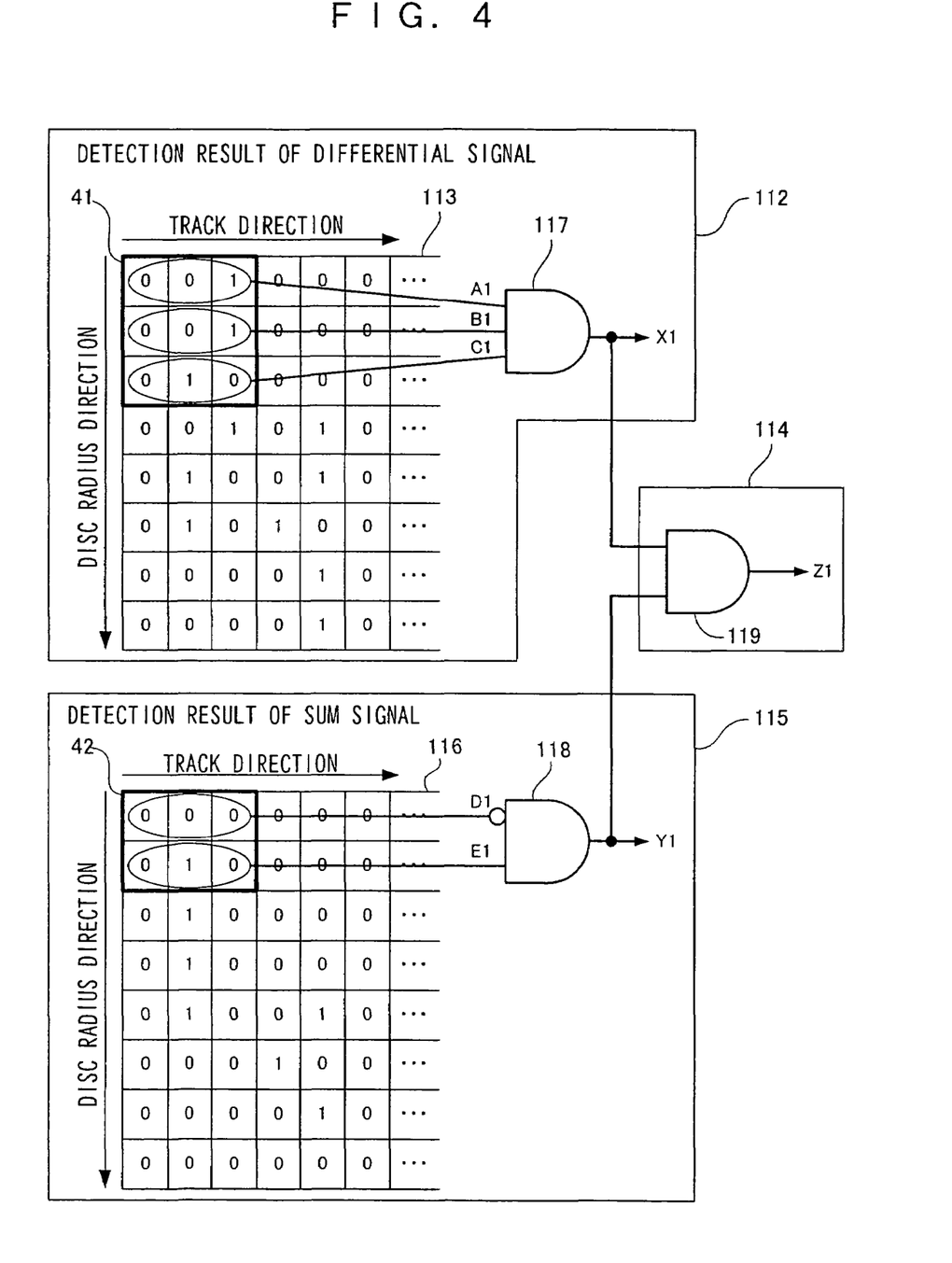
FIG. 4 is a diagram for explaining the operations of a differential signal detection circuit and a sum signal detection circuit in the optical analysis apparatus.
Figure 5:
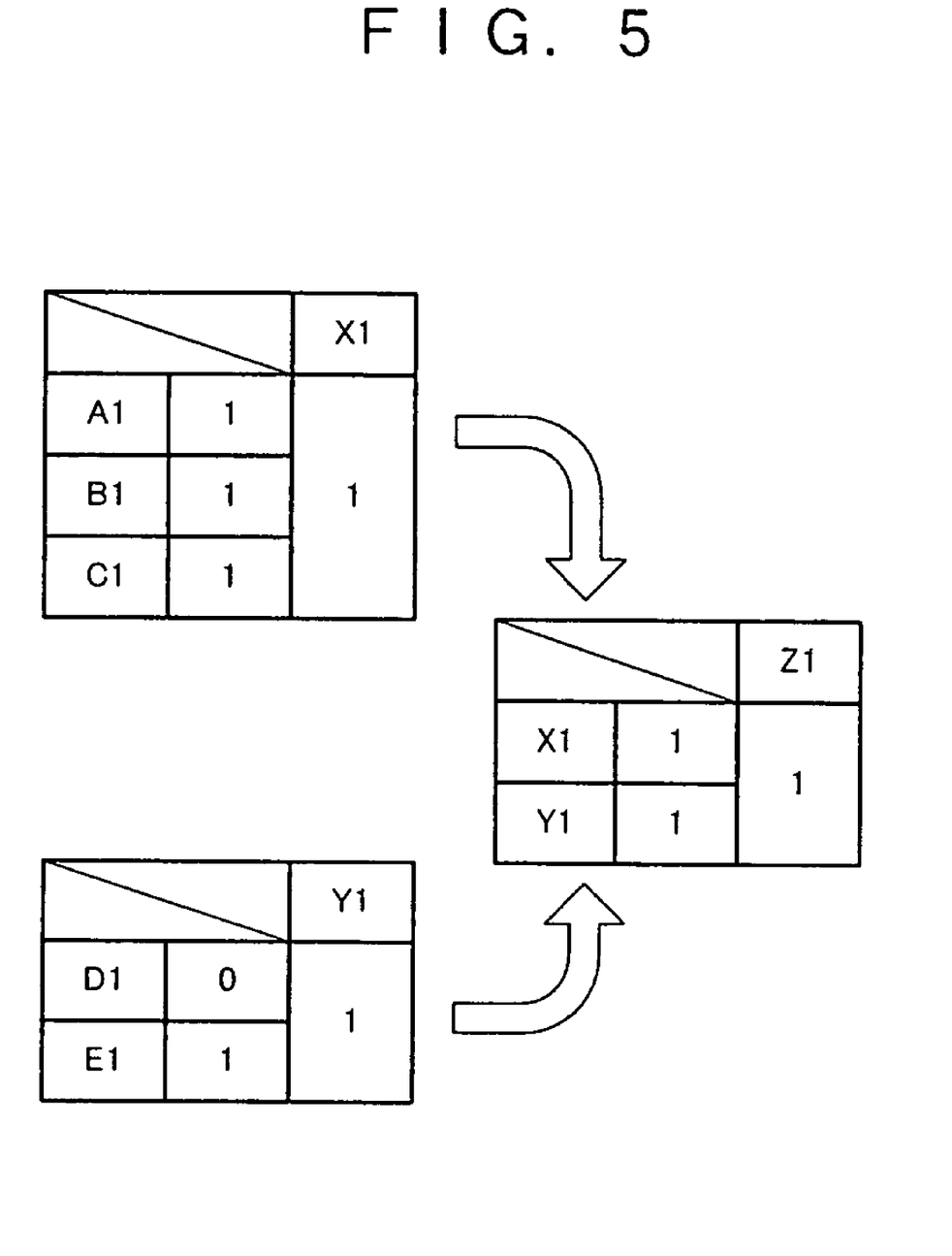
FIG. 5 is a diagram for explaining the operations of the differential signal detection circuit and the sum signal detection circuit in the optical analysis apparatus.

Referring to FIGS. 4 and 5, a state of the scanning window will be discussed below to explain the method of deciding the presence of a particle and the method of deciding the effectiveness of a particle.

"1" of A1, B1, and C1 in FIG. 5 indicates that at least one "1 (a particle is present)" is present in each row of the first scanning window 41 (M=3, N=A) of 3×A in the differential signal memory 113 of FIG. 4. Further, "0" indicates that "0 (a particle is not present)" is present in each row of the first scanning window 41 of 3×A in the differential signal memory 113. That is, data in each row of the first scanning window of 3×A indicates results inputted to an OR circuit. X1 in FIG. 5 indicates a result of inputting data from each row of the first scanning window of 3×A to an AND circuit 117 in response to the results of A1, B1, and C1 as shown in FIG. 4. When X1 is "1", the particle presence decision part 123 decides that a particle is present on the traced track. The particle presence decision result made by the particle presence decision part 123 is outputted to the particle detection circuit 114.

Further, "1" of D1 and E1 in FIG. 5 indicates that at least one "1 (a particle is effective)" is present in each row of a second scanning window 42 (m=2, n=A) of 2×A in the sum signal memory 116 of FIG. 4. Moreover, "0" indicates that "0 (a particle is ineffective)" is present in each row of the second scanning window 42 of 2×A in the sum signal memory 116. That is, FIG. 5 shows a result of inputting data in each row of the second scanning window 42 of 2×A to the OR circuit. Y1 in FIG. 5 indicates a result of inputting data obtained by passing D1 through a NOT circuit and the data of E1 to an AND circuit 118 as shown in FIG. 4. When Y1 is "1", the particle effectiveness decision part 128 decides that the counting of a particle on the traced track is effective. That is, a change from "0 (a particle is ineffective)" to "1 (a particle is effective)" is extracted from an adjacent area in the sum signal memory 116, and the effectiveness of counting a particle on the traced track is decided. The effectiveness decision result on the counting of a particle is made by the particle effectiveness decision part 128 and is outputted to the particle detection circuit 114.

Z1 indicates a result of inputting the data to an AND circuit 119 in the particle detection circuit 114 in response to the result X1 of the differential signal detection circuit 112 and the result Y1 of the sum signal detection circuit 115. When Z1 is "1", that is, when a particle is present and the counting of the particle is effective, the particle on the traced track is counted. FIGS. 4 and 5 show an embodiment of the counting of the particle.

Figure 6:
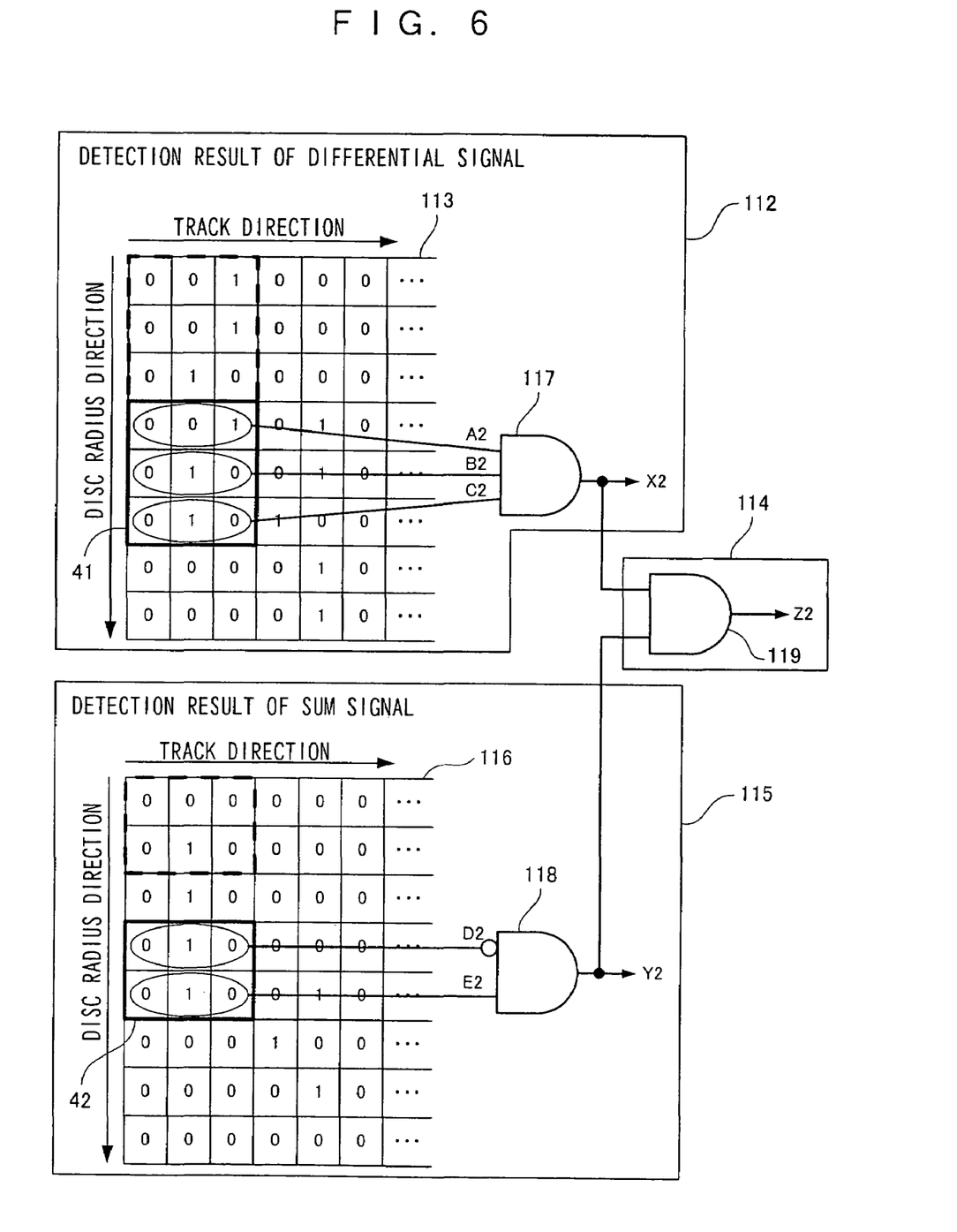
FIG. 6 is a diagram for explaining the operations of the differential signal detection circuit and the sum signal detection circuit in the optical analysis apparatus.

Subsequently, the first scanning window 41 of 3×A in the differential signal memory 113 and the second scanning window 42 of 2×A in the sum signal memory 116 are moved in the radius direction of the analysis optical disc 101 by a row width of the first scanning window 41 of 3×A. As has been discussed, a method of deciding the presence of a particle and a method of deciding the effectiveness of a particle will be described below (FIGS. 6 and 7).

Figure 7:
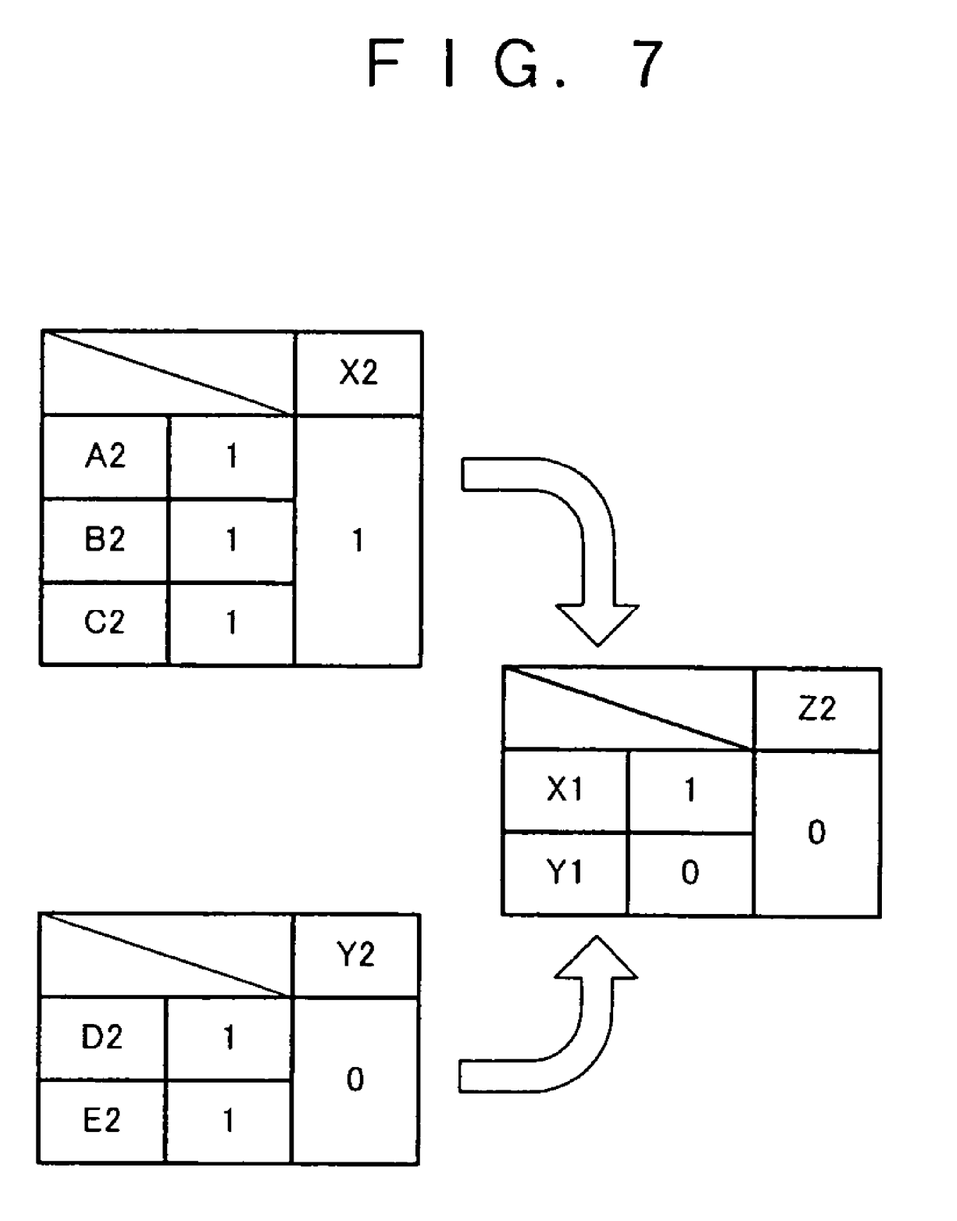
FIG. 7 is a diagram for explaining the operations of the differential signal detection circuit and the sum signal detection circuit in the optical analysis apparatus.

As with A1, B1, and C1 of FIG. 5, "1" of A2, B2, and C2 shown in FIG. 7 indicates a result of inputting data in each row of the first scanning window 41 of 3×A to an OR circuit in the differential signal memory 113. X2 in FIG. 7 indicates a result of inputting the data to the AND circuit 117 in response to the results of A2, B2, and C2 as shown in FIG. 6. When X2 is "1", the particle presence decision part 123 decides that a particle is present on the traced track.

As with D1 and E1 of FIG. 5, "1" of D2 and E2 in FIG. 7 indicates a result of inputting data in each row of the second scanning window 42 of 2×A to an OR circuit in the sum signal memory 116. As with Y1 of FIG. 5, Y2 in FIG. 7 indicates a result of inputting data obtained by passing D2 through a NOT circuit and the data of E2 to the AND circuit 118. When Y2 is "0", the particle effectiveness decision part 128 decides that the counting of a particle on the traced track is in effective. That is, a change from "0 (a particle is ineffective)" to "1 (a particle is effective)" cannot be extracted from an adjacent area in the sum signal memory 116, and the ineffectiveness of counting a particle on the traced track is decided.

Z2 is a result of inputting the data to the AND circuit 119 of the particle detection circuit 114 in response to the result X2 of the differential signal detection circuit 112 and the result Y2 of the sum signal detection circuit 115. When Z2 is "0", it is suggested that a particle is present but the counting of the particle is ineffective. That is, it is decided that a particle detected this time is the same as the previous detection and particles are not counted any more. FIGS. 6 and 7 show an embodiment in which no particle is counted.

In this way, the particle presence decision part 123 of the differential signal detection circuit 112 is caused to scan the differential signal memory 113 by means of the first scanning window 41 of 3×A, and the particle effectiveness decision part 128 of the sum signal detection circuit 115 is caused to scan the sum signal memory 116 by means of the second scanning window 41 of 2×A. Thus, it is possible to perform counting while confirming the effectiveness of a particle.

Figure 8:
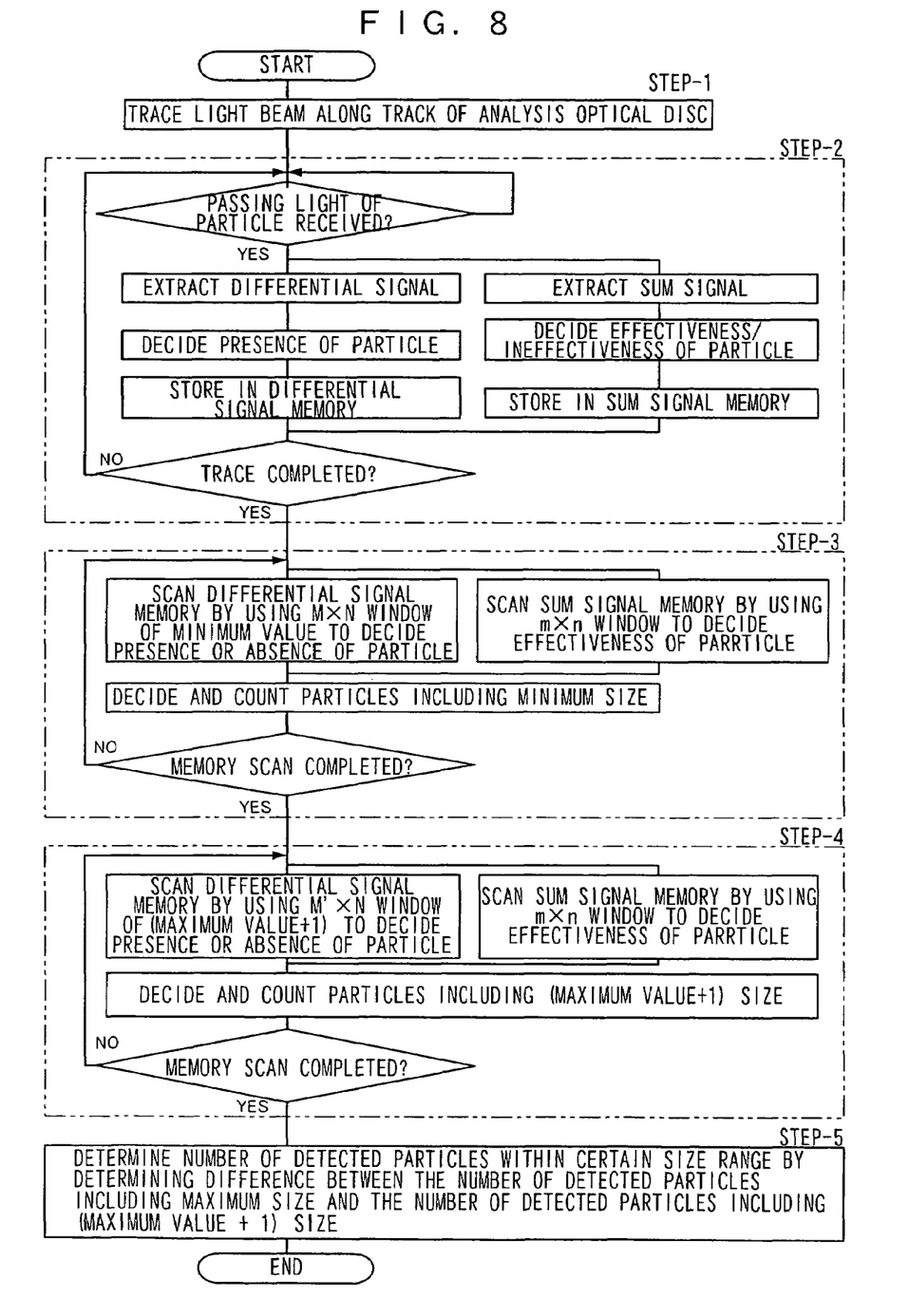
FIG. 8 is a flowchart for explaining a particle counting method of the optical analysis apparatus.

Referring to the flowchart of FIG. 8, a particle counting method of the analysis optical apparatus configured thus will be described below. As an example, the following will also describe the case where particles ranging in size from three to six tracks, which is a certain size range, are detected and counted on the analysis optical disc 101 having particles ranging in size from three to seven tracks disposed thereon (an example of various sizes).

Step-1

The disc motor 102 is driven by the disc motor control circuit 104 to rotate the analysis optical disc 101, and the feed motor 103 is driven by the feed motor control circuit 107 to move the pickup device 110 and the photodetector 111 in the horizontal direction. A light beam emitted from the pickup device 110 is traced along the track of the analysis optical disc 101.

Step-2

During the tracing, when the light beam emitted to the analysis optical disc 101 passes through a particle, the passing light is received by the bi-cell,photodetector 111. The differential signals 22 and 23 are extracted from the detection signals of the passing light of the photodetector 111 by the differential signal detection circuit 112, the presence of the particle is decided based on the extracted differential signals 22 and 23 by using a specific threshold value (first threshold value) as a criterion for deciding the presence of the particle, and the result is stored in the differential signal memory 113. At the same time, the sum signal detection circuit 115 extracts the sum signals 25 and 24 from the detection signals of the passing light of the photodetector 111, the effectiveness of the particle is decided based on the extracted sum signals 25 and 24 by using a specific value (second threshold value) as a criterion for deciding the effectiveness of counting the particle, and the result is stored in the sum signal memory 116.

Every time a particle is detected on the track in step-2, the presence of the particle is decided and the result is stored in the differential signal memory 113. At the same time, the effectiveness/ineffectiveness of the particle is decided and the result is stored in the sum signal memory 116. That is, in each scan, when it is decided that a particle is present, "1" is stored in the differential signal memory 113. When it is decided that no particle is present, "0" is stored in the differential signal memory 113 and the differential signal memory 113 is configured as a two-dimensional memory array. Similarly, in each scan, when it is decided that an effective particle is present, "1" is stored in the sum signal memory 116. When it is decide that an in effective particle is present, "0" is stored in the sum signal memory 116 and the sum signal memory 116 is configured as a two-dimensional memory array.

Step-3

After the tracing is completed, the differential signal memory 113 is scanned in the differential signal detection circuit 112 by using the first scanning window of M×N corresponding to the minimum value of detected particles within a certain size range, and the presence or absence of a particle is decided. At the same time, the sum signal memory 116 is scanned in the sum signal detection circuit 115 by using the second scanning window of m×n for capturing the extraction of a change from "0" to "1", and the effectiveness of counting the particle is decided. When it is decided that a particle is present and effective based on the results, the particle is counted as a particle including the minimum size of the certain size range, and the number of detected particles at this point is stored.

For example, the first scanning window 41 of 3×A corresponding to the minimum size (corresponding to three tracks) of detected particles is caused to scan the differential signal memory 113, the second scanning window 41 of 2×A is simultaneously caused to scan the sum signal memory 116, particles having a size of three tracks or more are detected, and the number of detected particles is stored.

The series of operations can prevent the same particle from being counted twice or more. That is, even in the case of a particle having a size of six tracks (a multiple of three tracks), counting can be correctly performed by deciding the effectiveness of counting the particle. However, a particle having a size of seven tracks, which is out of the certain size range (one track larger than the maximum size of detected particles), is counted twice or more at this point.

Step-4

Subsequently, the differential memory 113 is scanned in the differential signal detection circuit 112 by using a first scanning window of M'×N corresponding to a size one track larger than the maximum value of detected particles within the certain size range, and the presence or absence of a particle is decided. At the same time, the sum signal memory 116 is scanned in the sum signal detection circuit 115 by using the second scanning window of m×n for capturing the extraction of a change from "0" to "1", and the effectiveness of counting the particle is decided. When it is decided that a particle is present and effective based on the results, the particle is counted as a particle including a size one track larger than the maximum value of the certain size range, and the number of detected particles at this point is stored.

For example, the first scanning window of 7×A corresponding to a size one track larger than the maximum size (corresponding to seven tracks) of detected particles is caused to scan the differential signal memory 113, and the second scanning window of 2×A is simultaneously caused to scan the sum signal memory 116, particles having a size of seven tracks or more are detected, and the number of detected particles is stored.

Step-5

Subsequently, the number of detected particles within the certain size range is determined according to a difference between the number of detected particles including the minimum size of the particles in step-3 and the number of detected particles including a size one track larger than the maximum size of the particles in step-4.

For example, according to a difference between the number of detected particles having a size of three tracks or more and the number of detected particles having a size of seven tracks or more, the number of detected particles ranging in size from three to six tracks, which is the certain size range, is determined.

As described above, according to the present embodiment, among detected particles within the certain size range, the number of detected particles including the minimum size of the particles is determined by using the first scanning window corresponding to the minimum value and the second scanning window for capturing the extraction of a change from "0 (a particle is ineffective)" to "1 (a particle is effective)." Among the detected particles within the certain size range, the number of detected particles including a size one track larger than the maximum value of the particles is determined by using the first scanning window corresponding to a size one track larger than the maximum value and the second scanning window for capturing the extraction of a change from "0 (a particle is ineffective)" to "1 (a particle is effective)." The number of detected particles within the certain size range is determined by the difference between the numbers. Hence, even when particles serving as measured objects are varied in size, only a small number of scans is necessary in contrast to the conventional art, which uses a scanning window corresponding to a multiple of the minimum size of detected particles. Thus, it is possible to provide an optical analysis apparatus and a particle counting method whereby the number of particles serving as measured objects within the certain size range can be correctly determined in a short time among particles of various sizes in a specific area of the analysis optical disc 101.

According to the present embodiment, the presence of a particle is decided according to the amplitudes of the differential signals 22 and 23 in the differential signal detection circuit 112. The presence of a particle may be decided according to the periods of the differential signals 22 and 23. Similarly, the effectiveness of a particle is decided according to the amplitudes of the sum signals 25 and 24 in the sum signal detection circuit 115. The effectiveness of a particle may be decided according to the periods of the sum signals 25 and 24.

What is claimed is:

1. An optical analysis apparatus for determining the number of particles serving as measured objects within a certain size range, from particles of various sizes in a specific area of an analysis optical disc, the analysis apparatus, comprising:

a disc rotating device for rotating the analysis optical disc, a light-emitting device for emitting a light beam to the analysis optical disc, a scanner for driving the light-emitting device to scan the light beam having been emitted to the analysis optical disc, a light detector which is disposed on an opposite side of the analysis optical disc from the light-emitting device and has at least two receiving parts for receiving passing light of the light beam emitted from the light-emitting device to the analysis optical disc, the light-receiving parts having therebetween a boundary substantially orthogonal to a direction of scanning the light beam, a differential signal detection circuit constituted of a differential signal detection part which extracts a differential signal obtained by differentiating a signal of the passing light from the light-receiving parts of the light detector when the light beam passes through a particle, a differential signal memory, a differential signal decision part which decides whether a particle is present in the specific area of the analysis optical disc by using a first threshold value as a criterion for deciding presence of a particle based on the differential signal extracted by the differential signal detection part, and stores a result in the differential signal memory, and a particle presence decision part which scans the differential signal memory by using a first scanning window corresponding to a particle serving as a measured object within a certain size range, and decides the presence or absence of a particle serving as a measured object within the certain size range, a sum signal detection circuit constituted of a sum signal detection part which extracts a sum signal of the passing light from the light-receiving parts of the light detector when the light beam passes through a particle, a sum signal memory, a sum signal decision part which decides whether the analysis optical disc has a countable particle by using a second threshold value as a criterion for deciding whether a particle is countable based on the sum signal extracted by the sum signal detection part, and stores a result in the sum signal memory, and a particle effectiveness decision part which scans the sum signal memory by using a second scanning window for deciding effectiveness of counting a particle, and decides the effectiveness of counting a particle, and a particle detection circuit which determines the number of particles having a minimum size when the particle presence decision part and the particle effectiveness decision part decide that a particle having the minimum size is present among the particles serving as measured objects within the certain size range and counting of the particle is effective, and determines the number of detected particles having a size one scan larger than a maximum value and determines the number of detected particles within the certain size range based on a difference between the number of detected particles having the minimum size and the number of detected particles having a size larger than the maximum value by one scan, when the particle presence decision part and the particle effectiveness decision part decide that a particle having a size larger than the maximum value by one scan is present among the particles within the certain size range and the counting of the particle is effective.

2. The optical analysis apparatus according to claim 1, wherein the differential signal decision part has a presence result storing function of storing in the differential signal memory a mark indicating the presence of a particle when it is decided that a particle is present in each scan of the analysis optical disc, and storing in the differential signal memory a mark indicating absence of a particle when it is decided that a particle is absent, so that a two-dimensional memory array is constructed, and the sum signal decision part has an effectiveness result storing function of storing in the sum signal memory a mark indicating the presence of a countable particle when it is decided that a countable particle is present in each scan of the analysis optical disc, and storing in the sum signal memory a mark indicating the absence of a countable particle when it is decided that a particle is uncountable, so that a two-dimensional memory array is constructed.

3. The optical analysis apparatus according to claim 2, wherein the particle presence decision part has a function of detecting an array of the mark indicating the presence of a particle, from the two-dimensional memory array stored by the presence result storing function, by using the first scanning window of M×N (M indicates a size of the measured particle and N indicates a size corresponding to a displacement of a detection position on the analysis optical disc), and deciding the presence or absence of a particle, and the particle effectiveness decision part has a function of detecting a change from the mark indicating the absence of a countable particle to the mark indicating the presence of a countable particle, from the two-dimensional memory array stored by the effectiveness result storing function, by using the second scanning window of m×n (m indicates a value for capturing a change of the mark and n indicates a value equal to N), and deciding the effectiveness of counting a particle.

4. A particle counting method for determining the number of particles serving as measured objects within a certain size range, from particles of various sizes in a specific area of an analysis optical disc, the method comprising:

a step of emitting a light beam to the analysis optical disc and scanning the light beam on the analysis optical disc, a step of receiving passing light detected when the light beam passes through a particle, the passing light being received by being divided into at least two parts having therebetween a boundary substantially orthogonal to a direction of scanning the light beam, a step of extracting a differential signal and a sum signal from the received signal of the passing light, a step of deciding whether a particle is present on the analysis optical disc based on the differential signal by using a first threshold value as a criterion for deciding presence of a particle, and storing a result, a step of deciding whether a countable particle is present on the analysis optical disc based on the sum signal by using a second threshold value as a criterion for deciding whether a particle is countable, and storing a result, a step of scanning the stored presence decision result of a particle by using a first scanning window corresponding to a minimum value of particles serving as measured objects within a certain size range, and deciding presence or absence of the particle, a step of scanning the stored decision result on effectiveness/ineffectiveness of counting a particle by using a second scanning window corresponding to the effectiveness of counting a particle, and deciding effectiveness of counting a particle, a step of counting a particle having a minimum size when it is decided that the particle having the minimum size of particles within the certain size range is present and counting of the particle is effective, and storing the number of detected particles, a step of scanning the stored presence decision result of a particle by using a first scanning window corresponding to a size larger by one scan than a maximum value of the particles serving as measured objects within the certain size range, and deciding the presence or absence of a particle, a step of scanning the stored decision result on effectiveness/ineffectiveness of counting a particle by using a second scanning window corresponding to the effectiveness of counting a particle, and deciding the effectiveness of counting a particle, a step of counting a particle having a size larger than the maximum value by one scan when it is decided that the particle having a size larger by one scan than the maximum value of the particles within the certain size range is present and the counting of the particle is effective, and storing the number of detected particles, and a step of determining the number of detected particles within the certain size range based on a difference between the stored number of detected particles having the minimum size and the number of detected particles having a size larger than the maximum value by one scan.

* * * * *